United States Patent [19]

Togawa et al.

[11] 3,935,089
[45] Jan. 27, 1976

[54] OXYGEN SENSOR COATED WITH CATALYTIC MATERIAL

[75] Inventors: Kinmochi Togawa, Zushi; Kazuo Matoba, Yokohama; Hiroshi Takao, Kamakura; Yoshitaka Hata, Fujisawa, all of Japan

[73] Assignee: Nissan Motor Company Limited, Japan

[22] Filed: July 18, 1974

[21] Appl. No.: 489,539

[30] Foreign Application Priority Data

July 24, 1973  Japan............................... 48-83283

[52] U.S. Cl............................................. 204/195 S
[51] Int. Cl.²....................................... G01N 27/46
[58] Field of Search............ 204/195 S, 1 T; 324/29; 136/86 F

[56] References Cited

UNITED STATES PATENTS

| 3,300,344 | 1/1967 | Bray et al. | 136/86 F |
| 3,400,054 | 9/1968 | Ruka et al. | 204/1 T |
| 3,503,809 | 3/1970 | Spacil | 204/195 S X |
| 3,645,875 | 2/1972 | Record et al. | 204/195 S |

*Primary Examiner*—G. L. Kaplan
*Attorney, Agent, or Firm*—Robert E. Burns; Emmanuel J. Lobato; Bruce L. Adams

[57] ABSTRACT

One of the Pt electrodes of a concentration cell comprising a solid oxygen-ion electrolyte is coated with a porous inorganic material such as γ-type $Al_2O_3$ impregnated with an oxidation catalyst such as Pt so that oxidation reactions in a mixed gas to be measured may attain equilibrium before the gas comes into contact with the cell.

9 Claims, 4 Drawing Figures

OXYGEN SENSOR COATED WITH CATALYTIC MATERIAL

The present invention generally relates to a concentration cell comprising a solid oxygen-ion electrolyte, and more particularly to an oxygen sensor essentially consisting of such a cell and a catalytic coating deposited on one of the cell electrodes and to a method of making the same.

An oxygen concentration cell can be used to measure oxygen concentration in a mixed gas because the magnitude of the electromotive force (EMF) between two electrodes of such a cell is dependent on the difference in oxygen concentration in the two atmospheres surrounding the respective electrodes. When one of the electrodes is exposed to a reference gas such as air, variations of oxygen concentration in a sample gas can be detected continuously. Usually, a solid electrolyte such as an oxide of a tetravalent element, in which oxygen ions function as electron carriers, is chosen to make a cell suitable as a practical oxygen sensor.

This type of oxygen sensor is frequently employed in a control system for automatically controlling the air to fuel ratio (A/F) of a combustible mixture fed to an engine, particularly in automobile internal combustion engines to achieve top engine efficiency and/or to produce an innocuous or clean exhaust gas. The sensor is usually disposed in the exhaust system of the engine.

Since the A/F is in many cases near the stoichiometric ratio, the oxygen sensor is required to be highly sensitive to small deviations of the A/F about the stoichiometric value. In conventional oxygen sensors of this type, however, the variation of the EMF in response to the variation of the actual A/F in such a range is not sufficiently sharp to accurately judge whether the stoichiometric ratio is attained or not.

It is therefore an object of the present invention to provide an oxygen sensor which produces a sharp change in the magnitude of EMF in response to a variation of oxygen concentration in an exhaust gas resulting from a slight deviation of the A/F of a combustible mixture from the stoichiometric value.

It is another object of the invention to provide a method of making such a sensor.

According to the invention, an oxygen sensor comprises, like a conventional sensor, a layer of a solid oxygen-ion electrolyte, a first electrode formed on the electrolyte layer to communicate with a reference gas, and a second electrode formed on the opposite side of the electrolyte layer to communicate with the gas subject to measurement. Both electrodes are permeable to the gas. A coating of a porous inorganic material is formed on the second electrode, and the coating is impregnated with a catalyst for oxidation of oxidizable components in the gas to be measured. The coating has preferably a rough surface.

The solid electrolyte is selected from conventional solid solutions of $ZrO_2$—$CaO$, $CeO_2$—$CaO$ and $ThO_2$—$CaO$, the first being preferred, and the electrodes are preferably made of Pt. Examples of preferred coating material are $\gamma$-type $Al_2O_3$ and an aluminous cement, and the catalyst may be either Pt or Pd.

A method of making a porous and Pt-impregnated $\gamma$-type $Al_2O_3$ coating according to the invention comprises the steps of; depositing $\alpha$-type $Al_2O_3$ on a surface of a Pt electrode by means of a plasma injection, adjusting the temperature of the deposited $\alpha$-type $Al_2O_3$ to transform it into $\gamma$-type $Al_2O_3$, impregnating the $\gamma$-type $Al_2O_3$ with chloroplatinic acid, and heating the impregnated coating in a hydrogen atmosphere.

Other features and advantages of the invention will become clear from the following detailed description with reference to the accompanying drawing, in which.

Figure 1:
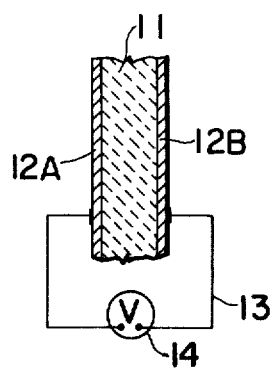
FIG. 1 is a partial sectional view of a conventional oxygen concentration cell.

In FIG. 1, a conventional oxygen concentration cell practicable as an oxygen sensor consists of a layer of a solid oxygen-ion electrolyte 11 such as zirconia, $ZrO_2$ stabilized with calcia, $CaO$ and two Pt electrodes 12A and 12B deposited on both surfaces of the layer 11. Both the electrodes 12A and 12B are permeable to gas and are connected to a potentiometer 14 via leads 13. When the electrodes 12A and 12B are exposed to air and, for example, to an engine exhaust gas, respectively, a potential difference is developed between the two electrodes 12A and 12B. The potential difference or EMF is determined by the Nernst's equation $$EMF = \frac{RT}{4F} \ln \frac{(PO_2)_1}{(PO_2)_2}$$

where R is the gas constant, T is the absolute temperature, F is the Faraday constant, $(PO_2)$ is the partial pressure of oxygen in a gas surrounding an electrode 12A or 12B, and the subscripts 1 and 2 refer to the reference air and the exhaust gas, respectively.

Figure 3:
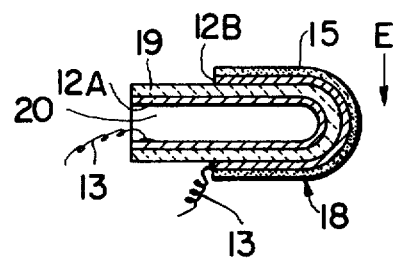
FIG. 3 is a graph showing qualitatively the variations of the magnitude of EMF when the cells of FIGS. 1 and 2 are exposed to an automobile engine exhaust gas as functions of A/F of a combustible mixture fed to the engine.

The curve I of FIG. 3 represents the variation of the EMF magnitude for the cell of FIG. 1 when the electrode 12B is exposed to an automobile engine exhaust gas and the A/F of a combustible mixture to feed the engine is varied about the stoichiometric ratio S. The curve III represents the oxygen concentration in the exhaust gas for reference. As is apparent from the curve I, there are two levels of the EMF magnitude, a higher level for an A/F range below S and a lower one for another range above S, and a level transfers gradually or mildly into the other level when the A/F is varied across S. Due to the mild slope of the curve I at the EMF level transition, it is very difficult to judge whether the A/F is just stoichiometric or slightly deviated therefrom.

The reason for such a mild transition of the EMF level is assumed as follows. Oxidation reactions in an actual engine do not attain equilibrium, so that oxygen concentration in the exhaust gas is always higher than theoretical values when an A/F lower than the stoichiometric ratio is employed. The platinum electrode 12B may act as a catalyst for reactions of oxygen contained in the exhaust gas with unburned hydrocarbons and carbon monoxide, but the catalytic effect of the electrode 12B is not considered strong enough to allow the reactions to attain equilibrium.

Figure 2:
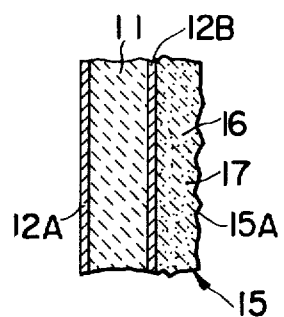
FIG. 2 is a partial sectional view of an oxygen concentration cell according to this invention.

Based on these analysis, the cell of FIG. 2, according to the invention has a coating 15 of a porous inorganic material 16, which is impregnated with a catalyst 17, on the outer surface of the electrode 12B. The solid electrolyte 11 and the electrodes 12A and 12B are similar to the conventional cell of FIG. 1. The catalyst 17 is selected from substances which catalyze oxidation reactions of oxidizable components in a gas to be measured such as an engine exhaust gas. The porosity of the coating 15 enhances the catalytic effect of the coating 15. The surface 15A of the coating 15 is preferably roughened to further enlarge the specific surface area thereof. The inorganic material 16 should be a material that is stable both chemically and thermally.

Figure 4:
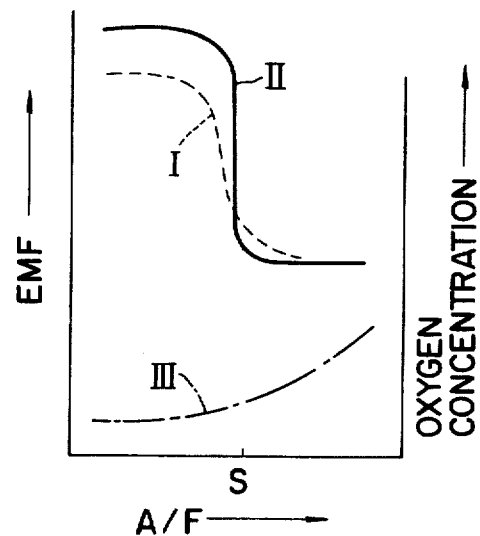
FIG. 4 is a sectional view of an oxygen sensor of this invention.

FIG. 4 shows an oxygen sensor 18 as a preferred embodiment of the invention. A top-sealed tube 19 made of a solid solution of 85 mole % $ZrO_2$ and 15 mole % CaO serves as the oxygen-ion electrolyte 11 of FIG. 2. As is known, CaO is a typical stabilizer for an oxide electrolyte such as $ZrO_2$. The Pt electrodes 12A and 12B are deposited on the inner and outer surfaces of the tube 19, respectively, and a pair of Pt wire leads 13 are connected to the electrodes 12A and 12B. The exterior electrode 12B is covered with the coating 15 of Pt-impregnated porous γ-type $Al_2O_3$.

The oxygen sensor 18 is produced by the following method according to the invention. The upper portion including the sealed end of the outer surface of the tube 19 as well as the inner surface is initially roughened by means of sand-blast. A platinum paste containing a fine powder of platinum in an organic binder is applied on the rough-finished portion and the inner surface of the tube 19, and then the tube 19 is baked at 1100°C for 2 hr to evaporate the binder and to form the electrodes 12A and 12B. After connection of platinum wire leads 13 to the respective electrodes 12A and 12B, α-type alumina is deposited on the exterior electrode 12B by means of plasma injection. The deposited α-type alumina transforms into porous γ-type alumina when the temperature is reduced. Alternatively, a paste containing γ-type alumina in a liquid binder is directly applied on the exterior electrode 12B followed by heating to evaporate the binder when requirement for the adhesion of the resulting coating 15 is not severest. Then, the γ-type alumina coating 15 is impregnated with chloroplatinic acid and is subsequently heated in a hydrogen atmosphere at 550°C for 3 hr to reduce the impregnating platinum ions to metallic platinum.

An aluminous cement containing calcium aluminate $Al_2O_3 \cdot CaO$ as a principal component is another excellent material 16 for the coating 15 of this invention. The watery cement is applied on the exterior electrode 12B and is hardened in a usual way to give a stable and porous coating 16. Also, a clay such as kaolin or bentonite substantially free from oxidation catalyst can be utilized. Such a clay is admixed with fine cellulose fiber or powder and water. Baking of the clay after application on the exterior electrode 12B causes the cellulose to disappear and gives an appropriate porosity to the clay coating 16.

The oxygen sensor 18 is installed in an exhaust pipe (not shown) of an engine by means of suitable attachment members (not shown) so that the coating 15 may be exposed to the stream of exhaust gas represented by the arrow E in FIG. 4. Air is passed in the interior 20 of the tubular sensor 18 as a reference gas for measuring the partial pressure or concentration of oxygen in the exhaust gas E.

The solid oxygen-ion electrolyte 11 in the present invention is not limited to the above $ZrO_2$-CaO, but may be selected from various conventional solid solution electrolytes composed of an oxide such as ceria $CeO_2$ and $ThO_2$ and a stabilizer such as calcia CaO. Pd may be used as the catalyst 17 instead of, or in combination with Pt.

Referring again to FIG. 3, the curve II represents the variation of the EMF magnitude for the cell of FIG. 2 according to the invention under the same condition as described before with respect to the curve I. As is apparent, curve II shows a very sharp transition from a high EMF level for a low A/F range to a low level at a point very close to the stoichiometric point S. Besides, the absolute EMF values in the higher level are larger than those of the curve I.

Such a characteristic may be considered to verify the assumption that the mild EMF level transition in the case of a conventional cell results from the presence of unreacted oxygen in the measured exhaust gas. The catalyst 17 impregnating the coating 15 has an extremely large specific surface area, so that the unreacted oxygen can be almost completely reacted with unburned hydrocarbons and carbon monoxide before the exhaust gas comes into contact with the exterior electrode 12B. In other words, the electrode 12B communicates always with the exhaust gas in an equilibrium state. Therefore, the curve II represents the excess or deficiency of oxygen in the combustible mixture more exactly than the curve I.

The sharp and great change in the EMF magnitude for the cell of FIG. 2 or the oxygen sensor 18 of the invention enables accurate judgement as to whether the stoichiometric mixing ratio is established or not. Accordingly, the amount of fuel supply to an engine in operation can be minutely controlled, or a predetermined A/F can be maintained with little change when the oxygen sensor 18 is used in a common control system for a fuel supply system of an engine.

What is claimed is:

1. An oxygen sensor to sense the difference in oxygen content between two gases, comprising a layer of a solid oxygen-ion electrolyte, a first metal electrode formed on a side of said electrolyte layer to communicate with a reference gas, a second metal electrode formed on the opposite side of said electrolyte layer to communicate with the gas being measured, both said first and second electrodes being permeable to gas, and a porous coating formed on said second electrode, said coating being of an inorganic material comprising at least a major amount of at least one refractory oxide and impregnated with a catalyst for oxidation of oxidizable components in said gas said refractory oxide comprises at least a substantial amount of $Al_2O_3$.

2. An oxygen sensor as claimed in claim 1, in which an exposed surface of said coating is roughened whereby the effective surface area is enlarged.

3. An oxygen sensor as claimed in claim 1, in which said electrolyte is a solid solution of CaO and an oxide selected from the group consisting of $ZrO_2$, $CeO_2$ and $ThO_2$, and said first and second electrodes are made of Pt.

4. An oxygen sensor as claimed in claim 1, in which said inorganic coating is γ-type $Al_2O_3$.

5. An oxygen sensor as claimed in claim 1, in which said inorganic coating material is a hardened aluminous cement containing $Al_2O_3 \cdot CaO$ as a principal component.

6. An oxygen sensor as claimed in claim 1, in which said inorganic coating material is a baked clay selected from the group consisting of kaolin and bentonite.

7. An oxygen sensor as claimed in claim 1, in which said catalyst is selected from the group consisting of Pt and Pd.

8. An oxygen sensor as claimed in claim 1, wherein said inorganic coating material is selected from the group consisting of γ-alumina, aluminous cement and baked clay.

9. An oxygen sensor comprising a tubular body made of a solid solution of $ZrO_2$ and CaO, an end thereof being sealed, a first Pt electrode formed on the inner surface of said body, a second Pt electrode formed on at least a portion of the outer surface of said body including the sealed end, both said first and second electrodes being permeable to gas, and a coating of porous γ-type $Al_2O_3$ formed on the surface of said second electrode, said coating being impregnated with Pt.

* * * * *